United States Patent [19]

West

[11] 4,260,780

[45] Apr. 7, 1981

[54] PHENYLMETHYLPOLYSILANE POLYMERS AND PROCESS FOR THEIR PREPARATION

[75] Inventor: Robert C. West, Madison, Wis.

[73] Assignee: The United States of America as represented by the Secretary of the Air Force, Washington, D.C.

[21] Appl. No.: 97,778

[22] Filed: Nov. 27, 1979

[51] Int. Cl.$^3$ ............................................... C07F 7/08
[52] U.S. Cl. .................................................. 556/430
[58] Field of Search ................. 260/448.2 D; 556/430

[56] References Cited

U.S. PATENT DOCUMENTS

| | | | |
|---|---|---|---|
| 2,563,005 | 8/1951 | Clark | 260/448.2 D |
| 4,052,430 | 10/1977 | Yajima et al. | 556/430 X |

*Primary Examiner*—Paul F. Shaver
*Attorney, Agent, or Firm*—Donald J. Singer; Cedric H. Kuhn

[57] ABSTRACT

A phenylmethylpolysilane polymer is prepared by the addition of a small amount of phenylmethyldichlorosilane to dimethyldichlorosilane and reduction of the resulting mixture. The polymer is a gum or meltable resinous material which has utility as a precursor for preparing silicon carbide fibers.

10 Claims, No Drawings

PHENYLMETHYLPOLYSILANE POLYMERS AND PROCESS FOR THEIR PREPARATION

RIGHTS OF THE GOVERNMENT

The invention described herein may be manufactured and used by or for the Government of the United States for all governmental purposes without the payment of any royalty.

FIELD OF THE INVENTION

This invention relates to phenylmethylpolysilane polymers. In one aspect, it relates to a process for preparing the polymers.

BACKGROUND OF THE INVENTION

As disclosed in "Polydimethylsilane", JACS, 71, 963-4 (1964), C. A. Burkhard synthesized permethylpolysilane polymer $(Me_2Si)_n$. The synthesis proceeded from dimethyldichlorosilane and sodium metal as shown by the following formula:

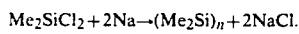

$Me_2SiCl_2 + 2Na \rightarrow (Me_2Si)_n + 2NaCl.$

The polymer formed in this manner is an infusible solid for which there is no known technical use.

More recently, in Japan, Yajima et al have shown that a permethylpolysilane polymer of the right molecular weight range can be drawn into fibers. Also the fibers upon heating are transformed into fibers of β-silicon carbide as shown by the following equation:

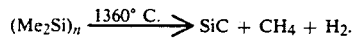

$(Me_2Si)_n \xrightarrow{1360° C.} SiC + CH_4 + H_2.$

The resulting fibers are extremely strong. The tensile strengths claimed exceed those of any known material, including carbon and boron fibers now used to reinforce high temperature materials, such as turbine blades, wing edges of high performance aircraft, and the like.

Yajima et al obtain their permethylpolysilane polymer by thermolysis of dodecamethylcyclohexasilane, $(Me_2Si)_6$. When $(Me_2Si)_6$ is heated to 400° C., it undergoes ring-opening polymerization to give polymers of various molecular weights. This product is solution fractionated since only polymers in the right molecular weight range can be spun or drawn into fibers.

It is a principal object of this invention, therefore, to provide a polymer that can be used directly to form fibers.

Another object of the invention is to provide a phenylmethylpolysilane polymer which undergoes thermolysis to silicon carbide.

Another object of the invention is to provide a process for preparing the phenylmethylpolysilane polymers.

Other objects and advantages of the invention will be apparent to those skilled in the art upon consideration of the accompanying disclosure.

SUMMARY OF THE INVENTION

The present invention resides in a phenylmethylpolysilane polymer having the following structural formula:

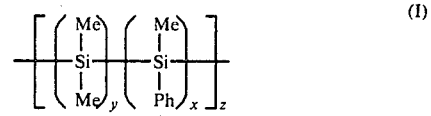

wherein Me is methyl, Ph is phenyl, the ratio of x to y varies from about 1:3 to 1:20, and z is an integer ranging from about 1 to 100. Depending upon the ratio of x to y and the value of z, the polysilanes can have a wide range of melting points and decomposition temperatures.

In one embodiment, the present invention resides in a process for preparing the phenylmethylpolysilane polymers. Broadly speaking, the process comprises the steps of adding phenylmethyldichlorosilane to dimethyldichlorosilane and reducing the resulting mixture with an alkali metal. The reaction that occurs is shown by the following equation:

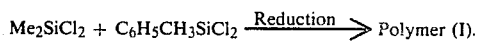

$Me_2SiCl_2 + C_6H_5CH_3SiCl_2 \xrightarrow{Reduction} Polymer (I).$

The reaction depicted by the above equation is carried out in a suitable solvent under a blanket of an inert gas. Any of the well known inert gases such as nitrogen, argon and helium, can be utilized. As a solvent (reaction medium), it is usually preferred to use tetrahydrafuran (THF) or xylene. As an alkali metal, sodium, potassium or a sodium-potassium alloy are usually utilized. The reactants ($Me_2SiCl_2$ and $PhCH_3SiCl_2$) are initially mixed in desired proportions after which the mixture is added to the solvent containing the alkali metal. The mole ratio of $PhMeSiCl_2$ to $Me_2SiCl_2$ usually ranges from about 1:3 to 1:20. As a result of the heat released by the exothermic coupling reaction, the solvent refluxes. After allowing the solution to reflux for at least 24 hours, e.g., from 24 to 48 hours, the reaction is quenched and solid polymer precipitates from the solution. Finally, the polymer is recovered by filtration and then dried. If desired, additional steps that are conventional in the art can be performed to purify the polymer product.

The polymers of this invention can be used as a starting material for making silicon carbide fibers. As disclosed by K. S. Mazdiyasni in commonly assigned, copending U.S. application Ser. No. 911,746, filed on June 2, 1978 and now issued on Dec. 4, 1979 as U.S. Pat. No. 4,177,230, the polymers may also be melted and absorbed into porous reaction sintered silicon nitride bodies. Thermolysis then converts the polymers to silicon carbide, thereby reinforcing and strengthening the porous body.

A more complete understanding of the invention can be obtained by referring to the following illustrative examples which are not intended, however, to be unduly limitative of the invention.

EXAMPLE I

Dried THF (500 ml) was added to a 2-liter, 3-neck flask fitted with an addition funnel, water condenser and stirrer. Na/K alloy (78% K) (95 ml) was added to the flask. A mixture of 121 ml (1.003 mole) of $Me_2SiCl_2$ and 21 ml (0.130 mole) of $PhMeSiCl_2$ (7.7 to 1 mole ratio $Me_2SiCl_2$ to $PhMeSiCl_2$) was added with stirring over a period of 2.5 hours. A cornflower blue color was obtained on addition of the chlorosilanes. The reaction mixture was allowed to reflux and stir for 36 hours.

The reaction was first quenched with 350 ml of hexane and then slowly and carefully with 200 ml of water. A white material of the consistency of feta cheese precipitated from solution. This material was allowed to dry for four days in an evaporating dish. The product was then ground up in a mortar and pestle to free any trapped solvent and dried in an oven (110° C.) for 4 hours. A brown-tinted polymer (78.8 g) was obtained with crystalline flecks appearing on its chunky surface.

The polymer was boiled in ethanol and dried to yield 70.9 g (96.1% overall yield) of a granular sugar-like material. The polymer does not melt below 280° C., but its surface wets at about 225° C. The infrared and nuclear magnetic spectra of the polymer are consistent with its structure as shown above.

EXAMPLE II $Me_2SiCl_2$ (103 ml) and $PhMeSiCl_2$ (35 ml) (3.9 to 1 mole ratio; 1 mole of silanes total) were mixed in an addition funnel under dry nitrogen purge. An oven-dried, 2-liter, 3-neck flask was charged with 750 ml of dry xylene (refluxed over Na metal for 24 hours) and 53.8 g of sodium metal (17% molar excess). The flask was fitted with the addition funnel, a motor stirrer, and reflux condenser, all under dry $N_2$ purge.

A heating mantle was used to heat the flask to about 100° C. to melt the sodium. The mixture of silanes was then added dropwise with vigorous stirring over a period of 20 minutes. During this time the heating mantle was shut off, and the xylene was allowed to reflux from the heat released by the exothermic coupling reaction. After the addition was complete, the solution was allowed to reflux for 36 hours with continuous stirring.

After 36 hours the reaction was quenched, first with 300 ml of methanol (Caution: Quenching too quickly causes the Na to catch fire.) and then 500 ml of a v/v mixture of 1 M HCl/EtOH. (Alternatively, aqueous $Na_2CO_3$ can be used in this step.) The objective is to quench the blue-purple color due to the defect NaCl trapped in the polymer. Several hours of stirring is often needed to rid the polymer of this color, leaving behind a white suspension.

The suspension was then filtered and the solid polymer was vacuum dried in a sublimer at room temperature. Rotovapping the filtrate down, extracting with water, and separating the organic layer (xylene solution) and rotovapping that down yields a small amount of additional polymer. The wet polymer yield was 87 g (115% yield), but drying in a 110° C. oven overnight reduced it to 70 g dry weight (92.5% yield). The polymer was slightly soluble in toluene, xylene and nitrobenzene, melted in the 300°–330° C. range, and had a gummy consistency. The infrared and nuclear magnetic spectra of the polymer are consistent with its structure as shown above.

As seen from the foregoing, the present invention provides a phenylmethylpolysilane polymer which can be used directly so that the synthesis of $(Me_2Si)_6$, thermal polymerization and fractionation, as required by prior art procedures, are rendered unnecessary. By varying the phenyl to methyl group ratio, the solubility and tractibility of the polymer can be varied. For example, a polymer made with a 4 to 1 mole ratio of $Me_2SiCl_2$ to $PhMeSiCl_2$ is gummy, melts at 300°–330° C., and is slightly soluble in toluene, xylene and nitrobenzene. On the other hand, any polymer made with a mole ratio greater than 5 to 1 is very crystalline and insoluble.

As will be evident to those skilled in the art, modifications of the present invention can be made in view of the foregoing disclosure without departing from the spirit and scope of the invention.

We claim:

1. A phenylmethylpolysilane polymer having the following structural formula:

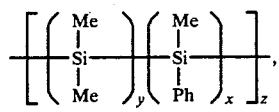

wherein Me is methyl, Ph is phenyl, the ratio of x to y varies from about 1:3 to 1:20, and z is an integer ranging from about 1 to 100.

2. A process for preparing a phenylmethylpolysilane polymer which comprises the steps of (a) mixing phenylmethyl dichlorosilane and dimethyldichlorosilane in which the mole ratio of phenylmethyldichlorosilane to dimethyldichlorosilane ranges from about 1:3 to 1:20; (b) adding the resulting mixture to a solvent containing an alkali metal reducing agent; (c) refluxing the resulting solution thereby causing a coupling reaction to occur; and (d) recovering a solid polymer from the said resulting solution.

3. A process in accordance with claim 2 in which the mole ratio of phenylmethyldichlorosilane to dimethyldichlorosilane is 1:3.9.

4. The process according to claim 2 in which the alkali metal reducing agent is sodium, potassium or a sodium-potassium alloy.

5. The process according to claim 4 in which the solvent is xylene or tetrahydrofuran.

6. The process according to claim 5 in which the solution is refluxed for at least about 24 hours.

7. The process according to claim 6 in which the solution is refluxed for a period of about 24 to 48 hours.

8. The process according to claim 5 in which the reaction is quenched at the end of the reflux period, thereby causing polymer to precipitate from solution; the polymer is separated from the solution; and the separated polymer is dried.

9. The process according to claim 8 in which the reaction is quenched first with methanol and then with an equal volume of 1 M hydrochloric acid and ethanol.

10. The process according to claim 8 in which the reaction is quenched first with hexane and then with water.

* * * * *